United States Patent [19]

Dentel et al.

[11] 4,349,488
[45] Sep. 14, 1982

[54] PROCESS FOR PRODUCING ESTERS OF 3,5-DIBROMO-4-HYDROXYBENZONITRILE

[75] Inventors: David A. Dentel; David C. Sanders, both of West Lafayette, Ind.

[73] Assignee: Great Lakes Chemical Corporation, West Lafayette, Ind.

[21] Appl. No.: 317,613

[22] Filed: Nov. 3, 1981

[51] Int. Cl.$^3$ .............................................. C07C 121/75
[52] U.S. Cl. .................................. 260/465 D; 71/105
[58] Field of Search .................................... 260/465 D

[56] References Cited

U.S. PATENT DOCUMENTS

| 3,349,111 | 10/1967 | Luckenbaugh | 260/465 F |
| 3,397,054 | 8/1968 | Hart et al. | 71/105 |
| 3,592,626 | 7/1971 | Heywood et al. | 71/105 |
| 3,671,556 | 6/1972 | Goldstick | 71/105 X |

FOREIGN PATENT DOCUMENTS

| 1375311 | 9/1964 | France . |
| 1067033 | 4/1967 | United Kingdom . |

OTHER PUBLICATIONS

Auwers and Reis (1896) reported In Cook, et al., "Biological Activity Of Various Halogenated Derivatives of Ioxynil," Northwest Weed Control Conf., vol. 19, pp. 321–323 (1965).
E. Muller, et al., Chem. Ber. 92 2278 (1959).
Carpenter et al., "Chemical and Biological Properties of Two New Herbicides–Ioxynil and Bromoxynil", *Weed Res.* (1964) 4 175–195.

*Primary Examiner*—Dolph H. Torrence
*Attorney, Agent, or Firm*—Kirkland & Ellis

[57] ABSTRACT

2,6-dibromo-4-cyanophenyl octanoates and other esters of 3,5-dibromo-4-hydroxybenzonitrile may be produced by reacting 4-hydroxybenzonitrile with bromine in the presence of an inert solvent and catalytic amounts of a basic heterocyclic aromatic compound or its hydrohalide, followed by removal of unreacted bromine and addition of octanoyl chloride or other acyl halide to the reaction mixture and recovery of the desired ester together with recyclable pyridine hydrohalide catalyst and solvent.

10 Claims, No Drawings

PROCESS FOR PRODUCING ESTERS OF 3,5-DIBROMO-4-HYDROXYBENZONITRILE

BACKGROUND OF THE INVENTION

1. Field of the Invention

This invention relates to the production of herbicidal esters of 3,5-dibromo-4-hydroxybenzonitrile and in particular to a novel process for producing such esters of high purity and in near quantitative yield.

2. Description of the Prior Art

The use of 3,5-dibromo-4-hydroxybenzonitrile as a herbicide is well established. Certain esters of 3,5-dibromo-4-hydroxybenzonitrile, especially the octanoate, have been used extensively as herbicides in the control of broad-leafed weeds, particularly in crop growing areas. These bromobenzonitrile derivatives have great economic value since they have been shown to be highly effective when applied to the growth of crops such as cereals, grasses, sugar cane, legumes, flax, linen, and various vegetables. These herbicides completely control undesirable vegetation at relatively low application rates without harming the crops and thus allow the crops to grow freely. The use of the 3,5-dibromo-4-n-octanoyloxybenzonitriles and their diiodo analogs as herbicides for treatment of broad-leafed weeds is disclosed in Haywood, et al., U.S. Pat. No. 3,592,626, granted July 13, 1971.

Although the esters have thus been shown to be highly effective, they have heretofore been produced only by incurring productivity penalties, which are aggravated by the expensive and cumbersome purifications that have heretofore been required.

3,5-Dibromo-4-hydroxybenzonitrile was first prepared by Auwers and Reis (1896) by a complex four step procedure starting with 4-hydroxybenzaldehyde, an uneconomical procedure involving bromination, formation of the aldoxime, dehydration with concomitant acetate formation and hydrolytic removal of the acetate.

Much later, E. Muller, et al., Chem. Ber. 92, 2278 (1959), described a procedure for bromination of 4-hydroxybenzonitrile with elemental bromine in methanolic acetic acid. The product produced by the Muller, et al., process was recovered by contacting the resulting bromination mixture with aqueous methanolic sodium hydrogen sulfite.

Luckenbaugh, U.S. Pat. No. 3,349,111, describes the production of 3,5-dibromo-4-hydroxybenzonitrile or its sodium salt by carrying out bromination with elemental bromine in an aqueous suspension, especially aqueous caustic, followed by a chlorine sparge.

French Pat. No. 1,375,311 describes bromination of hydroxybenzonitrile in acetic acid, obtaining 3,5-dibromo-4-hydroxybenzonitrile in 60% yield. The patent also suggests that by bromination with aqueous sodium hypobromite the product may be obtained in 78% yield.

While the production of 3,5-dibromo-4-hydroxybenzonitrile itself has only been obtained by difficult procedures or with poor yield and overall economics, the methods heretofore known for obtaining the herbicidally more active esters have been fraught with even greater difficulty.

The two principal methods used to obtain esters of 3,5-dibromo-4-hydroxybenzonitrile have involved either reaction with an organic anhydride in the presence of a condensing agent or reaction of bromobenzonitrile with an acid halide in the presence of at least stoichiometric quantities of a base such a pyridine or a quarternary ammonium salt.

Thus, Hart, et al., U.S. Pat. No. 3,397,054, describes the production of alkanoyl derivatives of halo-substituted 4-hydroxybenzonitriles by reaction of 3,5-dibromo-4-hydroxybenzonitrile with the appropriate acid anhydride in pyridine as a solvent. The deficiencies of this procedure include the fact that only one-half of the acid anhydride is incorporated into the product, while the remaining acid must be removed as an impurity. Also, the use of pyridine as a solvent presents recovery difficulties and problems of toxicity and cost.

French Pat. No. 1,375,311 describes the production of 2,6-dibromo-4-cyanophenyl octanoate by reacting purified 3,5-dibromo-4-hydroxybenzonitrile with octanoyl chloride in excess pyridine, again presenting serious problems of toxicity, cost and recovery.

As a result of the foregoing disadvantages of the prior art acid anhydride and acid halide processes, Goldstick, U.S. Pat. No. 3,671,556, suggests that herbicidal esters of 3,5-dihalo-4-hydroxybenzonitriles could be obtained by slow direct addition of dry, solid dihalohydroxybenzonitrile to hot liquid acid halide. However, even this method presents difficulties, including plant scale solids handling problems, foaming, long reaction cycles, and the necessity for isolating and recovering purified dihalohydroxybenzonitrile intermediates.

Accordingly, a primary object of this invention is to obtain a process for simply and economically converting 4-hydroxybenzonitrile to esters of 3,5-dibromo-4-hydroxybenzonitrile of exceptionally high purity and in near quantitative yield.

A further object is to provide a process of the character described in which the intermediate 3,5-dibromo-4-hydroxybenzonitrile is reacted in situ to produce the resultant ester without being recovered or purified.

A still further object is to obtain a process of the character described in which large quantities of hazardous and expensive materials such as pyridine need not be employed.

A still further object is to provide a process of the character described in which catalytic amounts of pyridine or pyridine hydrohalides are employed with pyridine hydrohalides being recovered and recycled.

SUMMARY OF THE INVENTION

The foregoing and other objects, advantages, and features of the present invention may be achieved with a process for producing esters of the formula:

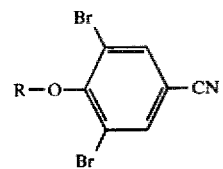

where R is an acyl group derived from aliphatic and haloaliphatic carboxylic acids containing 3 to 12 carbon atoms and mononuclear aromatic and haloaromatic acids.

The process comprises the steps of reacting 4-hydroxybenzonitrile with bromine at elevated temperature in the presence of an inert solvent and a catalytic amount of a basic aromatic heterocyclic compound or hydrohalide thereof as a catalyst. Thereafter any unreacted bromine is removed from the reaction mixture, and an acyl halide of the formula R-X, where R is defined above and where X is Cl or Br, is contacted with the reaction mixture under anhydrous conditions while maintaining an elevated temperature, with the ester thereby produced being recovered from the reaction mixture.

By carrying out the process of this invention in the foregoing manner, it is possible to obtain a 3,5-dibromo-4-hydroxybenzonitrile ester of high purity and in near quantitative yield.

DETAILED DESCRIPTION OF THE PREFERRED EMBODIMENTS

In accordance with this invention, esters of 3,5-dibromo-4-hydroxybenzonitrile are obtained in a single reaction from 4-hydroxybenzonitrile starting material in the presence of a compatible inert solvent and catalytic amounts of a basic heterocyclic aromatic compound or hydrohalide thereof such as pyridine or pyridine hydrohalide.

During the first or bromination stage of the reaction, 4-hydroxybenzonitrile is reacted with elemental bromine in the presence of catalyst and inert solvent at elevated temperatures. After the bromination reaction has completed, any unreacted bromine is removed, for example, by addition of a reducing agent such as formic acid.

After removal of unreacted bromine and any water that is present in the reaction system, the second stage of ester formation is carried out by contacting an acyl halide with the reaction mixture at elevated temperatures. Removal of water enables ester formation to occur under anhydrous conditions.

On conclusion of the ester formation, the reaction mixture is cooled, thereby precipitating catalyst, which may be recovered by filtration and reused. The desired 2,6-dibromo-4-cyanophenyl ester may then be recovered in very high purity and in near quantitative yield.

More specifically, it has been found that the reaction may be successfully carried out using basic heterocyclic aromatic compounds or hydrohalides thereof (e.g., pyridine hydrochloride or pyridine hydrobromide) as the catalyst. Other suitable catalysts include alkyl pyridines such as 2-,3-, or 4-methylpyridine and halo-substituted pyridines such as 2-, 3-, or 4-chloro- or bromopyridines and their hydrohalides. Pyridine and its hydrohalides are preferred catalysts in accordance with this invention.

Catalytic amounts of the catalyst are employed (i.e., amounts significantly less than stochiometric amounts.) Specifically, no more than about 0.2 mole of catalyst per mole of 4-hydroxybenzonitrile is required.

Chlorobenzene has been found to be an especially useful solvent, in that, under the conditions of the reaction, it successfully maintains the intermediate 3,5-dibromo-4-hydroxybenzonitrile as well as the resulting ester in solution, thereby allowing the entire process to be conducted in a single reaction vessel without separation and/or purification of the intermediate. Other inert solvents exhibiting similar solvent characteristics may be employed.

Desirably, the bromination stage is carried out at the reflux temperature of the solvent, i.e., at a temperature in the range of about 134° C. in the case of chlorobenzene. The second or ester formation stage of the process is also carried out at elevated temperatures, although the process is preferably carried out at temperatures somewhat below reflux temperatures in order to aid in the control of foaming due to hydrogen halide evolved during ester formation. Thus, the esterification is preferably carried out at a temperature in the range of about 120°-130° C., preferably at about 125°-130° C.

During the bromination reaction an excess of elemental bromine is preferably provided in the reaction mixture. Although the exact amount of bromine is not critical, it has been found that bromine in an amount ranging from about stoichiometric up to about a 25% excess may be employed, preferably about a 5-15% excess.

During ester formation, a small excess of acyl halide is preferably employed. The exact amount of acyl halide is not critical although significant benefits are not obtained with acyl halide excesses greater than 5 or 10% above the stoichiometric amount.

During each of the bromination and ester formation steps, the reaction mixture is desirably maintained at the specified elevated temperature during a hold period following addition of each reactant in order to permit the bromination and ester formation reactions to go to completion.

As noted also, product recovery following the ester formation reaction is initiated by cooling the reaction mixture so as to cause the pyridine hydrohalide catalyst to precipitate. Desirably, cooling to about 25° C. causes precipitation to occur. Filtration then permits the pyridine salt to be recovered in reuseable form.

The remaining mixture of the ester of 3,5-dibromo-4-hydroxybenzonitrile and solvent is then separated by appropriate means such as vacuum distillation, thereby permitting the solvent also to be recycled.

The desired ester derivative is thus obtained at purities ranging to 98% and in near quantitative yields.

Preferably, the ester formation is carried out in an inert gas environment such as in a nitrogen atmosphere. It has been found to be especially helpful to employ a nitrogen sparge to facilitate removal of the hydrogen halide generated during the second stage of the reaction, thereby enhancing process efficiencies.

As noted, the reaction of this invention can be carried out to produce any of a wide number of esters of 3,5-dibromo-4-hydroxybenzonitrile by varying the acyl halide employed. In particular, acyl halides of the formula R-X may be used, where X is chlorine or bromine and R is an acyl group derived from aliphatic and haloaliphatic carboxylic acids containing 3 to 12 carbon atoms and from mononuclear aromatic and haloaromatic carboxylic acids.

More particularly, acyl halides derived from an aliphatic carboxylic acid, preferably one containing 3 to 12, especially 3 to 8, especially 8, carbon atoms may be used. Particularly suitable are acyl groups derived from n-octanoic, 2-ethylhexanoic, propionic and n-butyric acids. The acid from which the acyl group is derived may be unsaturated.

The acyl groups in this class can be unsubstituted or substituted. If the groups are substituted, they are preferably substituted with one or more halogens, particularly chlorine or bromine atoms, preferably in the alpha-position. Examples of acyl groups containing such substituents are alpha, alpha-dichloropropionyl and trichloroacetyl groups. They may also be substituted with a phenoxy group containing at least one halogen substituent and further substituted by one or more halogen atoms or methyl groups. Examples of acyl groups containing such a substituent are 4-chloro-2-methylphenoxyacetyl, gamma-(4-chloro-2-methylphenoxy)-n-butyryl, 2,4-dichlorophenoxyacetyl, gamma-(2,4-dichlorophenoxy)-n-butyryl and 2,4,5-trichlorophenoxyacetyl.

Acyl halides derived from aromatic carbocyclic carboxylic acids, which are preferably mononuclear, may also be used. Examples of acyl groups within this class are benzoyl groups. These acyl groups may also be halogen substituted.

Preferred esters that may be produced in accordance with this invention are those obtained by the reaction of n-octanoyl chloride and 2-ethylhexanoyl chloride with 3,5-dibromo-4-hydroxybenzonitrile, that is, the preferred esters are 2,6-dibromo-4-cyanophenyl n-octanoate and 2,6-dibromo-4-cyanophenyl 2-ethylhexanoate.

As noted, the esters produced in accordance with this invention have utility in controlling the growth of broad-leafed weeds.

EXAMPLE I

2,6-Dibromo-4-cyanophenyl Octanoate

A. Bromination

Chlorobenzene (1250 ml), pyridine (12.5 g, 0.16 mole) and 4-hydroxybenzonitrile (297.8 g, 2.5 moles) were charged to a three-liter reaction vessel, and the resulting mixture was brought to reflux (about 134° C.) Bromine (839 g, 5.25 moles) was charged to the reactor over a one-and-one-half hour period. Hydrogen bromide evolved during the bromination and was collected in a caustic scrubber.

After a one-half hour hold at reflux (about 136° C.) formic acid (25 g of 90%) was added over a thirty-minute period. The mixture was maintained at reflux (120° C.) for one-half hour. Water (contained in the formic acid) was removed by azeotropic distillation, causing the pot temperature to increase from 120° to 130° C.

B. Ester Formation

The reactor contents were then adjusted to 130° C. and n-octanoyl chloride (427 g, 2.625 moles) was charged over a one-half hour period. A nitrogen sparge removed the by-product hydrogen chloride. Formation of the ester was completed by holding the sparge.

C. Product Recovery

The reaction mixture was cooled to about 25° C. and filtered to recover the pyridine hydrobromide. (The recovered salt is recyclable to a subsequent reaction.) Chlorobenzene was removed by vacuum distillation (100° C. (at 1 mm/Hg)), affording 1003.5 g of product (nearly quantitative yield) in 98% purity.

EXAMPLE II

2,6-Dibromo-4-cyanophenyl Octanoate

The procedure of Example I was repeated with the exception that 20 g of recovered, recycled pyridine hydrobromide was substituted for the pyridine catalyst of Example I. Product yield was 1000 g of better than 97% purity product.

EXAMPLE III

2,6-Dibromo-4-cyanophenyl 2-Ethylhexanoate

The procedure of Example I was carried out except that 2-ethylhexanoyl chloride (427 g, 2.625 moles) was substituted for octanoyl chloride of Example I. One thousand and five grams of 2,6-dibromo-4-cyanophenyl 2-ethylhexanoate (a nearly quantitative yield) was obtained. The product was of excellent purity.

I claim:
1. A process for producing 2,6-dibromo-4-cyanophenyl esters of the formula:

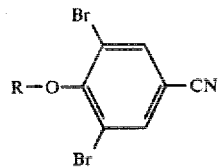

where R is a member selected from the group consisting of an acyl group derived from aliphatic and haloaliphatic carboxylic acids containing 3 to 12 carbon atoms and mononuclear aromatic and haloaromatic carboxylic acids, comprising the steps of:
  reacting 4-hydroxybenzonitrile with bromine at elevated temperatures in the presence of an inert solvent and a catalytic amount of a basic heterocyclic aromatic compound or hydrohalide thereof;
  thereafter removing unreacted bromine from the reaction mixture;
  contacting the reaction mixture under anhydrous conditions while maintaining an elevated temperature with an acyl halide of the formula R-X, where X is a member selected from the group consisting of chlorine and bromine and where R is given above; and
  recovering the ester thereby produced from the reaction mixture.

2. A process, as claimed in claim 1, wherein the inert solvent is chlorobenzene.

3. A process, as claimed in claim 1, in which the bromination reaction is carried out at an elevated temperature up to about the reflux temperature of the reaction mixture.

4. A reaction, as claimed in claim 1, wherein the reaction mixture is contacted with acyl halide in the presence of a inert gas.

5. A process, as claimed in claim 1, in which the reaction mixture is contacted with acyl halide at an elevated temperature below the reflux temperature of the reaction mixture.

6. A process, as claimed in claim 1, wherein the basic heterocyclic aromatic compound or hydrohalide thereof is a member selected from the group consisting of pyridine and pyridine hydrohalides and further comprising the step of recovering recyclable pyridine hydrohalide from the reaction mixture.

7. A process, as claimed in claim 1, and further comprising the step of recovering recyclable solvent from the reaction mixture.

8. A process, as claimed in claim 1, wherein R is an n-octanoyl group and the ester is 2,6-dibromo-4-cyanophenyl n-octanoate.

9. A process, as claimed in claim 1, in which R is a 2-ethylhexanoyl group and the product is 2,6-dibromo-4-cyanophenyl 2-ethylhexanoate.

10. A process for producing 2,6-dibromo-4-cyanophenyl n octanoate comprising the steps of:
  reacting 4-hydroxybenzonitrile with an excess of bromine in chlorobenzene solvent at an elevated temperature up to about reflux temperature and in the presence of a catalytic amount of a member selected from the group consisting of pyridine and pyridine hydrohalides;

holding the reaction mixture at about reflux temperature to complete the reaction;

thereafter removing unreacted excess bromine from the reaction mixture by adding a reducing agent to the mixture;

separating and removing water from the reaction mixture;

contacting an excess of n-octanoyl chloride with the reaction mixture under anhydrous conditions while maintaining an elevated temperature below the reflux temperature of the reaction mixture;

holding the reaction mixture at an elevated temperature below reflux to complete formation of the ester;

recovering separately 2,6-dibromo-4-cyanophenyl octanoate of high purity, recyclable pyridine hydrobromide, and recyclable chlorobenzene.

* * * * *